(12) United States Patent
Mays (10) Patent No.: US 8,534,618 B2
(45) Date of Patent: Sep. 17, 2013

(54) CPAP TUBE DELIVERY DEVICE

(76) Inventor: Audie L. Mays, Killen, AL (US)

( * ) Notice: Subject to any disclaimer, the term of this patent is extended or adjusted under 35 U.S.C. 154(b) by 258 days.

(21) Appl. No.: 13/199,260

(22) Filed: Aug. 24, 2011

(65) Prior Publication Data

US 2013/0047987 A1 Feb. 28, 2013

(51) Int. Cl.
*F16M 11/00* (2006.01)
(52) U.S. Cl.
USPC .............. 248/161; 248/75; 248/121; 248/157
(58) Field of Classification Search
USPC .............. 248/75, 58, 121, 125.1, 125.8, 158, 248/161, 157
See application file for complete search history.

(56) References Cited

U.S. PATENT DOCUMENTS

| 5,239,995 A | 8/1993 | Estes et al. |
| 6,224,027 B1 | 5/2001 | Johnson et al. |
| 6,854,694 B1 | 2/2005 | Van Etten |
| 7,040,581 B2 * | 5/2006 | Noelke et al. ................... 248/75 |
| 7,744,043 B2 | 6/2010 | Otinger |
| 8,181,918 B2 * | 5/2012 | McCloud ........................ 248/81 |
| 2004/0056159 A1 * | 3/2004 | Schulze ..................... 248/125.1 |
| 2007/0170318 A1 * | 7/2007 | Gunerman ................... 248/68.1 |
| 2008/0078397 A1 | 4/2008 | Scott et al. |
| 2008/0185359 A1 | 8/2008 | Baxter |

* cited by examiner

*Primary Examiner* — Amy J. Sterling
(74) *Attorney, Agent, or Firm* — Stephen R. Chapman (57) ABSTRACT

A CPAP oxygen delivery device wherein a tube system eliminates excess hose and wherein a base connector positioned in the support frame may be in a T- or cross-configuration and the cross-configuration allows a supplemental therapeutic material to be delivered, and wherein the pitch of an adjustable arm may be varied to alter the vertical position of the CPAP mask.

10 Claims, 9 Drawing Sheets

CPAP TUBE DELIVERY DEVICE

FIELD OF THE INVENTION

The invention is generally related to home therapy devices, although hospital and other institutional uses are anticipated. It is more specifically related to devices to provide continuous positive airway pressure (CPAP) to individuals suffering from obstruction sleep apnea, and is specifically directed to devices that reduce inconvenience and other problems inherent with excessive lengths of air delivery hoses that bind bedding, restrict movement, and may result in displacement of the air mask, thereby neutralizing the desired therapeutic benefits of the CPAP system.

INTRODUCTION

Sleep apnea is a potentially dangerous disorder in which afflicted individuals repeatedly stop breathing while sleeping. Such sleep disruptions deny an individual of necessary rest and may lead to more serious health problems, including congestive heart failure.

The most common form of sleep apnea is obstruction sleep apnea (OSA) caused by relaxation of throat muscles resulting in blockage of the throat (air passage way). The condition it is more prevalent among over weight males age 40 years and older.

The use of devices to provide continuous positive airway pressure (CPAP) to individuals suffering from sleep apnea has become a medically favored, effective remedy for this annoying, potentially serious condition. CPAP therapy requires afflicted individuals to wear a mask or comparable device that is connected to an air source at night The mask, per se is annoying an interrupts sleep. The added inconvenience of excessive air delivery hoses between the pump and mask binding and restricting normal movement or tugging and pulling/displacing the mask disrupts sleep and may interrupt the recommended flow of air and the benefits of the therapy.

A variety of devices that support the air deliver hose and with varying effectiveness address issues of limiting excessive air hose and reduce the annoyance associated with binding and restricting movement and displacing the air mask caused by excessive lengths of delivery hose. Devices include systems that allow hose length to be mechanically varied as an individual moves, with excessive hose retracted to avoid binding the individuals. The retraction exerts annoying pulling on the mask that may become a serious limitation by pulling and displacing the mask.

The CPAP system comprises three major elements: an air pump to deliver a specified volume of air under constant and low, but positive pressure to an individual; a fitted face mask worn by the individual through which air is delivered to the nose/mouth of the individual; and a length of hose that connects the pump/air supply to the face mask. For effective therapeutic use of the CPAP system, the mask is fitted and secured around the face with a harness or strap system to minimize loss of air and/or reduction of delivery pressure of the air to the patient and to ensure air delivery to the nostrils.

CPAP therapy is effective; however, it is not without inconveniences and discomfort to patients. Two related problems are (1) proper fitting of the mask to ensure a soft-seal of the mask and desired deliver of air and (2) discomfort of wearing the mask while sleeping plus the annoyance/discomfort of excessive lengths of the delivery hose on the bed, pillow or tangled in the bedding or clothing and resultant pulling on the hose/mask and face.

PRIOR ART

Both popular, retail advertisements and United States patents and patent applications suggest continuing efforts to improve CPAP systems. Efforts include addressing the unresolved problems of supporting the hose system so as to minimize discomfort to the patent and pulling the mask as a result of excessive lengths of hose that may bind bedding or clothing.

For example, the Walter Drake Mid-Spring (2011) catalog (Walter Drake, Oskosh Wis. 54906; www.wdrake.com) describes an array of devices related to sleep apnea therapy: specially designed pillows and pillow cases to minimize snoring (a common symptom of sleep apnea) (#331226); a chin strap to minimize blockage of the airway (#337020); and a CPAP hose holder (#333958). The hose holder comprises a base arm to secure the device between the mattress and bedspring, a vertical arm to position the hose above the patient, a swing arm to which the hose is attached such that the mask is positioned over the patient and the hose is minimally in contact with the bedding/bed/clothing. The hose is attached to the swing and as a result, the hose may pull the mask as the patient moves.

The April, 2011 Fresh Finds catalog (Fresh Finds, North Wales, Pa. 19454; www.FreshFinds.com) describes a hose holder similar to the previously described Drake hose holder (#45863, CPAP Hose Holder). Both devices are adjustable in height and fold for storage, both are anchored between the mattress and bedspring, and the hose is connected to the device, with the section of hose holding the mask positioned above the patient.

The Harriet Carter Spring 2011 Sales catalog (Harriet Carter, North Wales, Pa. 19455; www.harrietcarter.com) offers a seemingly identical hose holder (CPAP Hose Holder, #E2548). See also BroGho HoseBuddy B&H Manufacturing, available through CPAP Supply USA, Midlothian, Va. The hose support device is similar to other devices described, with the hose connected to a vertical support arm that extends to support the mask above the patient, and the device is an anchored between the mattress and bedspring.

In addition to published catalogs as cited above, numerous web sites offer CPAP devices and supplies, including hose support devices, many of which are similar in structure and function to the devices described above. See for example CPAP Supply USA Midlothian, Va. 23112 (cpapsupplyusa-.com).

The CPAP Hose Wrangler constitutes a significant variation from the bed mounted vertical support hose holder devices. The devices features a pair of reels mounted on the bed side with the CPAP hose passing across both reels such that the length of the hose from the last reel to the mask can be adjusted by pushing/pulling on the hose by force exerted in moving the face mask, thereby minimizing excessive hose to tangle bedding and clothing. The hose is "apparently" weighted to minimize the pull necessary to extract/retracted the hose, but force on the mask to move the hose remains an issue, and the mechanical device (reels) take space at bed height (CPAPhosewrangler.com).

The Cozy Hose Boss represents an additional hose support variation. A pair of retractable reels is attached to the wall above bed. Each reel is attached by a cord to a separate point on the hose, and one or both points can be lowered by extending the cord from one or both reels thereby lowering the mask, or effectively extending the hose or raised by allowing the reels to retract and effectively raise the hose, effectively shortening the hose. Constant retractile pressure is maintained on the mask, and extension requires additional force to lower (extend) the hose. The convenience of control of hose length may easily be offset by the constant pulling force on the mask. (See www.cpapsupplyusa.com).

CPAP therapy devices have been the subject of a variety of US utility patents. U.S. Pat. No. 5,239,995 issued Aug. 31, 1993 to Estes, et al. discloses and claims an apparatus that allows alternating application of high and low positive airway pressure through a controlled pumping system. It does not address hose support.

A variety of patents and patent applications address hose stands and technology to reduce the inconvenience and possible harm arising from excessive lengths of CPAP hoses.

U.S. patent application Ser. No. 11/836,081 filed May 1, 2001 by Edward Baxter discloses and claims a foldable, CPAP hose support device similar to several previously described in several commercial publications (See Collections Etc., Spring 2011 or Fresh Finds April, 2011). The CPAP hose is supported by a foldable arm structure that is anchored between the mattress and bedspring with the hose attached to the arm structure that extends above the patients head so that the excess hose does not bind bedding and clothing. A rubber cord extends the length of the length of the arm structure and connects the foldable segments, and the hose is connected to the arm structure by a loop in the cord. The length of the hose can effectively be increased by stretching the cord by pulling on the hose, against the loop/cord; the hose is retracted when the pressure pulling) is released. This pulling exerts undesired pull on the face mask as previously discussed regarding other hose holders.

U.S. patent application Ser. No. 11/862,525 filed Sep. 27, 2007 by Scott, et al. discloses and claims a multi-purpose support system; supporting tubing, wires, and hoses, including CPAP hoses. The device comprises a base, support arm and flexible arm with hose attachment fasteners. Common with all similar devices, a major purpose of this device is to support and hold tubes, hoses, and wires out of the way from interference with or by a patient. This general purpose device illustrates the commonality among many designated CPAP hose holders.

U.S. patent application Ser. No. 6,224,027 issued May 1, 2001 to Johnson, et al. discloses and claims a tubular, flexible, telescoping oxygen tube (hose) support stand. The tube or hose is attached to the telescoping tube, and height of the tube support point is adjusted by adjusting the length of the flexible, telescoping tube.

In U.S. Pat. No. 6,854,694 filed Feb. 15, 2005, Van Etten discloses and claims a device that allows tube or hose to be pulled through it in only one direction. Although this may the purpose and function is to allow the length of a tube of hose, such as a tracheal tube to freely be lengthened to avoid a patient inadvertently pulling the tube out of position. By design, it allows the accumulation of excess tubing or hose, and for that reason is not markedly adapted to serve as a CPAP hose support.

U.S. Pat. No. 7,744,043 issued Jun. 29, 2010 to Otinger discloses a CPAP hose tender in which one end of a support arm is connected to a clamp device to connect the hose tender to a bed or other appropriate point, and the other end of the arm is formed into a hose engaging section with a cantilevered section over which the hose is positioned and along which it may travel a limited distance to increase (or decrease) the effective length of the hose without requiring excessive length be added and which allows additional hose to be pulled over the cantilevered section to further increase or decrease the hose length available to accommodate movement by the patient.

There appears to be room in the art for a CPAP riser tube delivery system in which the mask is connected by a section of hose to a riser tube delivery system that is connected by a section of hose to the CPAP air pump and in which changing the pitch of an adjustable tube to which the mask is attached by a short length of hose determines the height of the mask, and rotating the adjustable tube establishes the horizontal orientation of the mask thereby eliminating the need for excessive lengths of hose.

SUMMARY OF THE INVENTION

A first purpose and objective of the invention is a device that minimizes the loose or free hose connecting the CPAP mask to the air pump.

A second purpose and goal of the invention is a jointed, rigid tube system that replaces the majority of the tube required in currently available CPAP systems.

A third purpose and goal of the invention is a support frame with an anchor that removeably attaches the tube system to a bed and that provides support and positioning of the tube system and of a base connector which is removeably positioned and secured to the support frame.

A fourth purpose and objective of the invention is base connector that comprises an output arm, an air input arm, and a drain arm access arranged in a T-configuration and that may be arranged in a cross-configuration to further comprise a supplemental input arm (or access port).

A fifth purpose and objective of the invention is a swivel connection that allows an adjustable tube to move upward/downward (to adjust the pitch) in relation to horizontal thereby adjusting the height of the mask attached to the tube relative to the reclining position of user.

A sixth purpose and goal of the invention is a jointed tube system in which risers are detachably connected by a segmented connector.

These and other purposes, objectives, and goals are achieved by a CPAP support device consisting of an open, box-like base with an anchor that removable connects the base to a bed, a base connector in a T-configuration and comprising an upper output arm, a first (air) input arm, and access drain arm; the base connector may assume a cross-configuration in which case it also includes a second, supplemental input arm; the first riser of the tube system connects that riser to the output arm and to a connector that joins the first riser to a second riser; the second riser is connected to an adjustable connector, and the adjustable connector is also connected to an adjustable tube that is attached to the mask hose that delivers air to the mask; the adjustable connector allows the adjustable tube to be rotated in an arc such that the relative position of the connection of the mask hose (hence of the mask) can be altered without changing the actual length of the mask hose; the first input arm is connected to an arm connector that is connected by hose to the CPAP air pump; the access drain arm is connected to a lower drain arm connector that is closed by a cap or threaded plug, and the second input arm is connected to an arm connector is connected by hose to a device (such as an atomizer, cartridge or pump) to deliver supplemental therapeutic materials; the first riser, input arm connectors, and lower drain arm connector all traverse adjacent elements of the support frame (the top, first side and second side, and bottom), are held in position in the support frame.

EXAMPLES

Figure 1A:
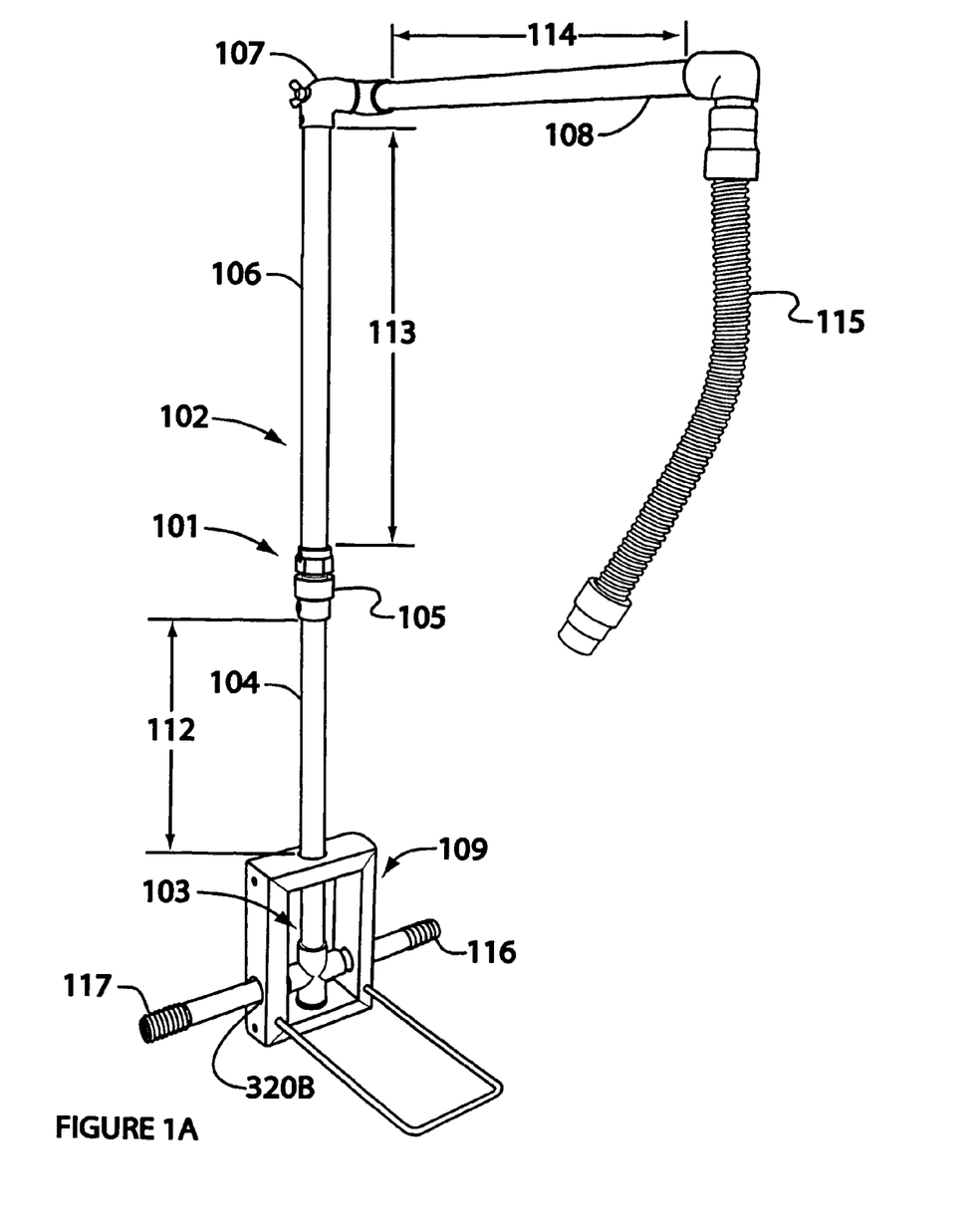
FIG. 1A is an overview of the CPAP Riser Tube Delivery System.

FIG. 1A provides an overview of the CPAP tube delivery system 101. The CPAP tube delivery system 101 comprises three major elements the tube system 102, the frame connector 103, and the support frame 109. The tube system 102 comprises a first riser 104, a riser connector 105, a second riser 106, an adjustable connector 107, and an adjustable tube 108.

Figure 1B:
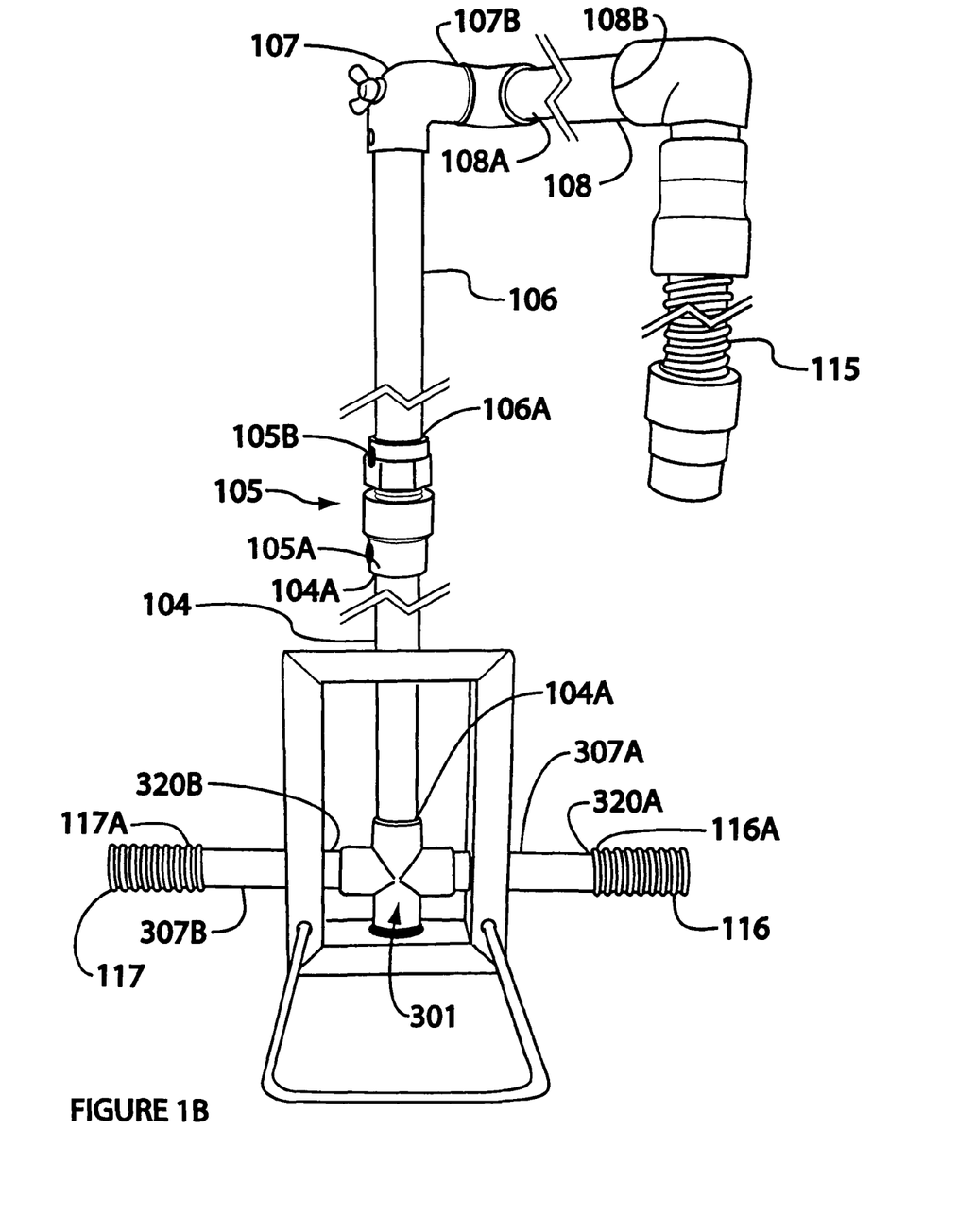
FIG. 1B provides details of the CPAP Riser Tube Delivery System.

The first riser 104, the second riser 106, and the adjustable tube 108 have respective lengths 112, 113, and 114. By way of example, not of limitation, the length of the first riser 112 and the second riser 113 commonly are equal and vary from 1.0 to 2 feet (30.5 to 61 cm), and the length of the adjustable tube 114 varies from 1.0 to 2.5 feet (30.5 to 75 cm). The first riser connector 105 physically and functionally connects the first riser and the second riser 106. The adjustable tube connector 107 physically and functionally connects the second riser 106 and the adjustable tube arm 108.

Figure 2:
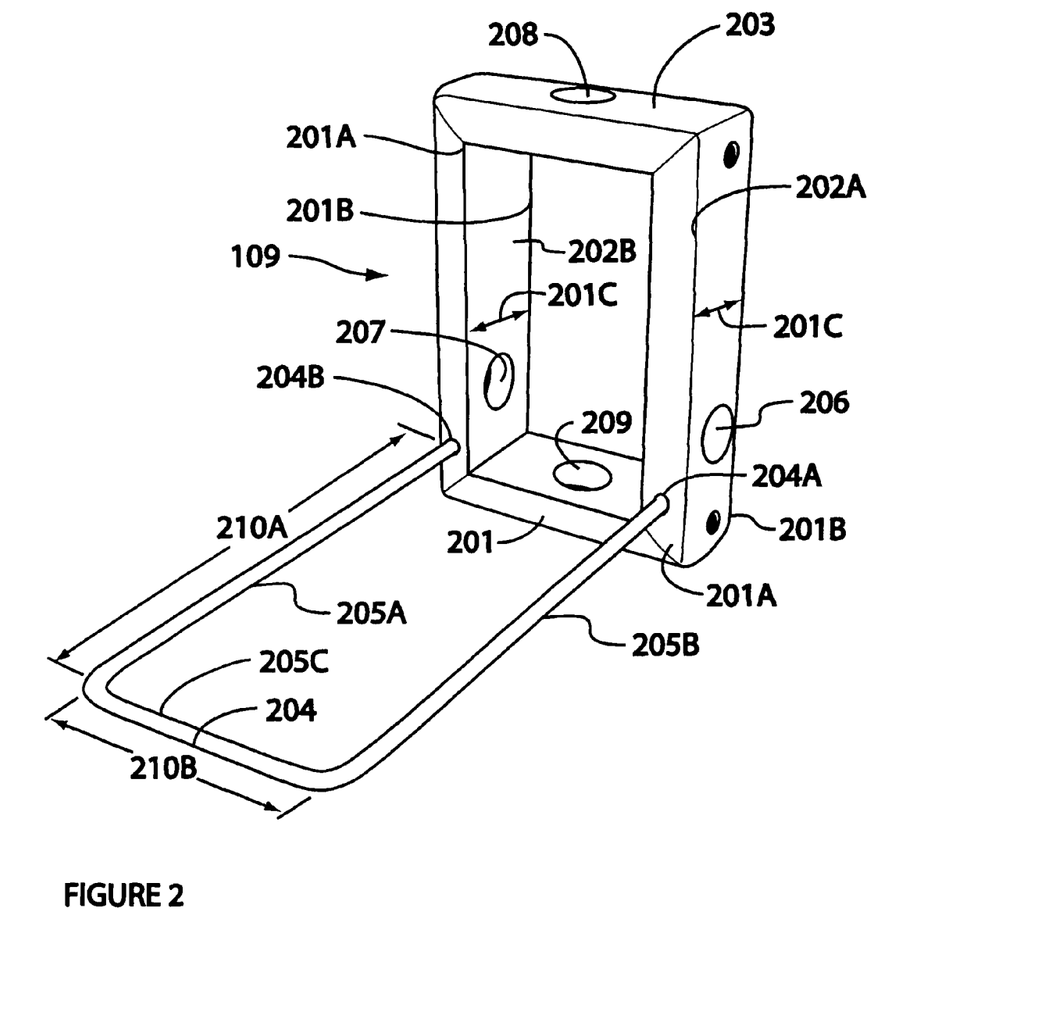
FIG. 2 provides details of the support frame.

The frame 109, as illustrated in FIG. 2 comprises a four-sided, open box structure with a bottom 201, a first 202A and a second 202B side wall, and a top 203. The frame further comprises an anchor 204. The top 203 comprises a first, traverse passage 208.

The first side 202A and the second side 202B walls comprise respectively a second, traverse passage 206 and a third, traverse passage 207. Similarly, the bottom 201 comprises a fourth, traverse passage 209.

Each member of a pair of anchor sockets 204A and 204B respectively traverse the first 202A and the second 202B side wall of the frame from the front edge 201A to the back edge 201B, spanning the width 201C of the of the corresponding side walls 202A and 202B.

The anchor 204 is fabricated from a single length of metal rod 0.25 inch (0.63 cm) in diameter (or comparable, heavy, inflexible wire).

The anchor 205 comprises a bridge section 205C and a first 205A and a second 205B anchor leg. The first 205A and second 205B anchor legs are parallel, equal in length 210A, and extend from opposite ends of the bridge section 205C. By way of example, not limitation, the length 210A of the anchor legs 205A and 205B varies from 6 to 18 inches (15 to 45 cm). The length 210B of the bridge 205C is effectively equal to the distance between the members of the pair of anchor sockets 204A and 204B.

The anchor 204 is mechanically connected to the first and second sides 202A and 202B of the open box-like structure. The end of each anchor leg 205A and 205B engages and is physically inserted into and secured in a the corresponding anchor socket 204A and 204B. The anchor legs 205A and 205B are held in place by friction and may be readily pulled from the sockets by hand, without tools to facilitate disassembling the frame.

Figure 3A:
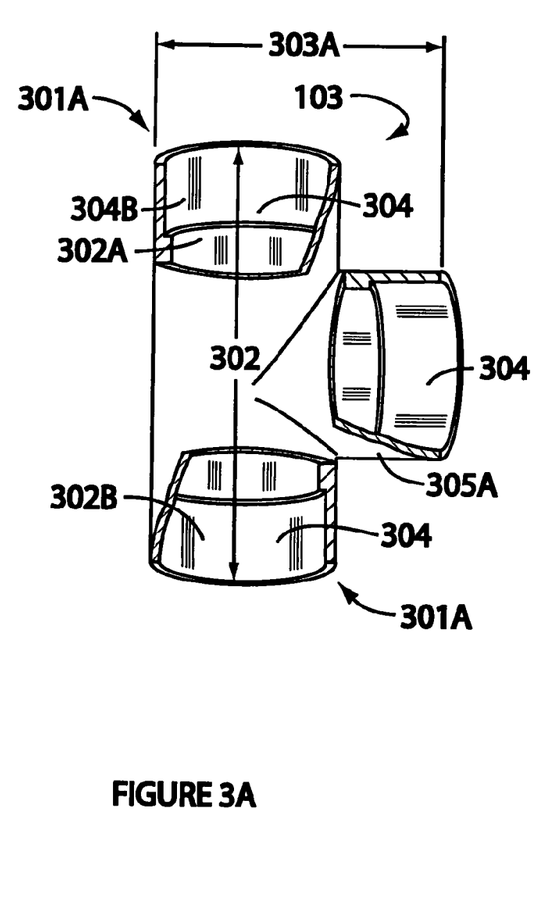
FIG. 3A illustrated the T-configuration of the frame connector.
Figure 3B:
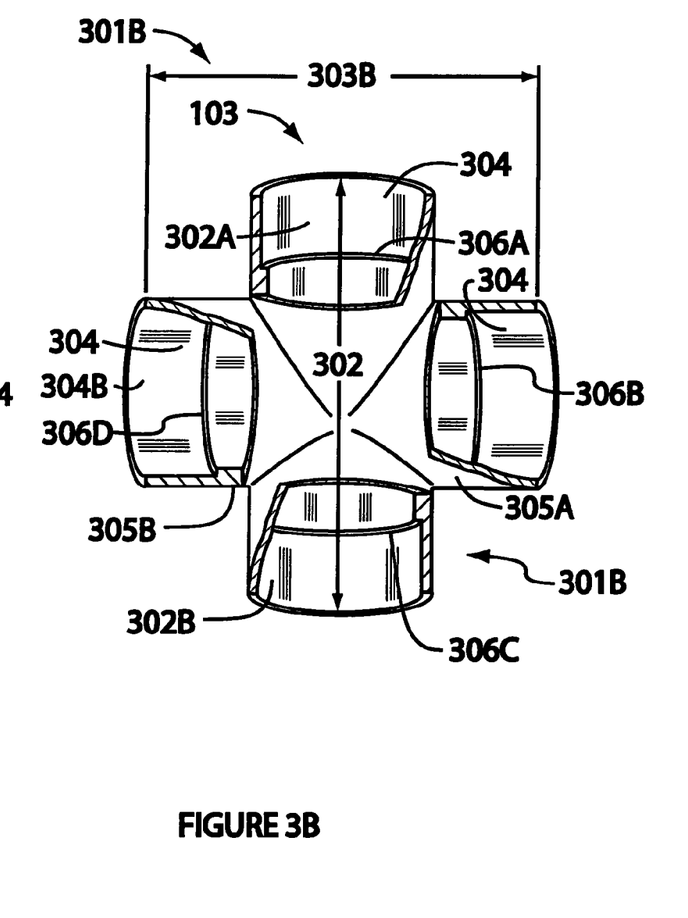
FIG. 3B illustrates the cross-configuration of the frame connector.
Figure 3C:
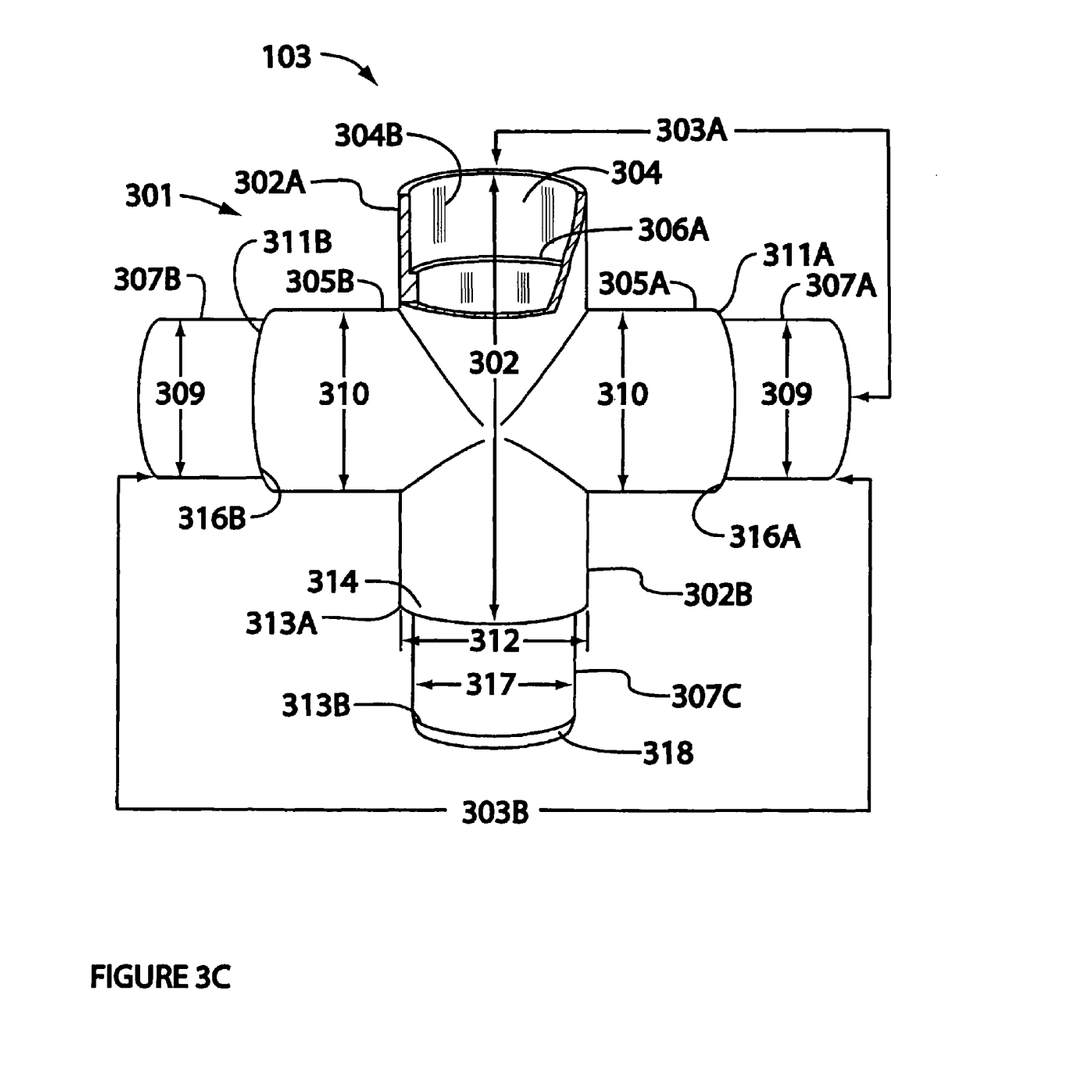
FIG. 3C compares details of both configurations of the frame connector.

The frame connector 103 comprises the connector body 301. The connector body 301A/B comprises a vertical axis and element 302 and a horizontal axis and element 303A/B. The connector body assumes one of two basic shapes or configurations: a T-configuration 301A or a cross configuration 301B (compare FIG. 3A with FIG. 3B). The vertical axis and element 302 is effectively the same for the T-configuration 301A and the cross-configuration 301B. The vertical axis and element 302 comprises the upper output arm 302A and the lower drain access arm 302B. FIG. 3A illustrates the T-configuration, and FIG. 3B illustrates the cross-configuration. FIG. 3C combined FIG. 3A and FIG. 3B for convenience of comparisons.

The horizontal axis and element 303A of the T-configuration 301A of the connector body 301 comprises the first input arm 305A. The horizontal axis and element 303B of the cross-configuration of the connector body 301B comprises the first input arm 305A and the second input arm 305B.

The interior 304 of the connector body 301 as shown in FIG. 3A and FIG. 3B is defined and limited by an interior wall surface 304B of the structural wall 304A of the connector body 301. The interior 304 of the connector body 301 comprises a single, contiguous open core or chamber functionally and physically connecting the vertical axis and element 302 and the horizontal axis and element horizontal axis and element 302 (including both the T-configuration 301A and the cross-configuration 301B).

The horizontal axis and element 303A/B may comprise only the first input arm 305A or the first input arm 305A and the second input arm 305B. In either case, the first input arm 305A is the essential air input arm and the second input arm 305B is for the input of supplemental, but non-essential therapeutic materials. The configuration with only the first input arm is defined as the T-configuration, and the configuration with both the first input arm 305A and the second input arm 305B is defined as the cross-configuration. Both the T-configuration 305A and the cross-configuration 305B structurally and functionally have a common vertical axis and element 302, with effectively identical interiors 304, interior wall structure 304B, structural walls 304A, and identical upper output arms 302A, as well as identical lower drain arm access 302B.

The inner diameter 310 of the first 305A and the second 305B input arms is equal and fractionally less that the corresponding outer diameter 309 of the first 307A and the second 307B input arm connectors. The first end 311A of the first input arm connector 307A engages the connector end 316A of the first input arm 305A and is held frictionally tight in place; the first end 311B of the second input arm connector 307B similarly engages the connector end 316B of the second of the second input arm 305B and is held frictionally tight in place. The upper output arm 302A of the connector body 301 comprises a first ledge structure 306A that circumscribes the circumference of the interior wall surface 304B of the upper output arm 302A and is effectively part of than surface, as shown in FIG. 3C.

Figure 3D:
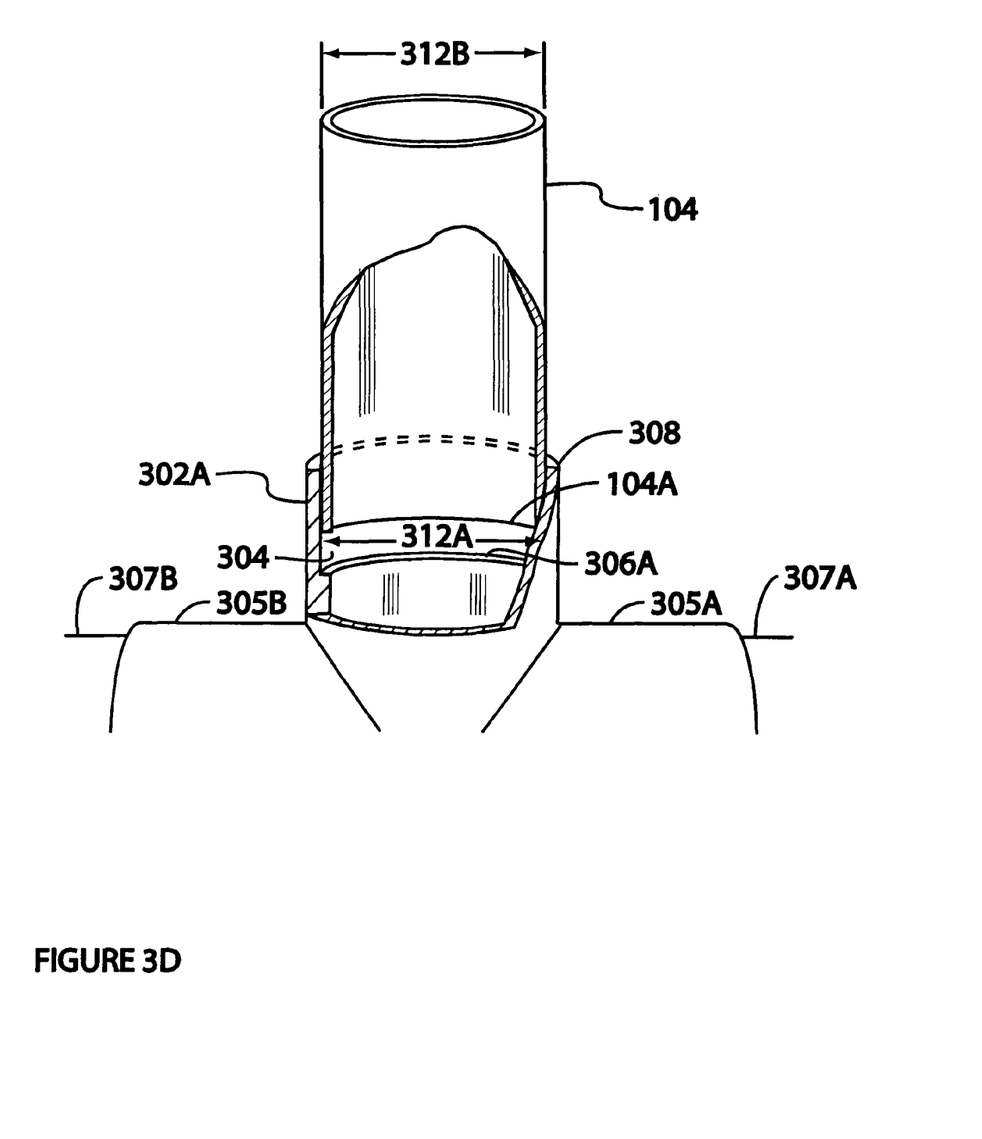
FIG. 3D illustrates the engagement of a riser to the frame connector.

As shown in FIG. 3D, the outer diameter 312B of the first riser 104 is fractionally less than the inner diameter 312A of the upper output arm 302A. The first end 104A of the first riser 104 engages the receptacle end 308 of the upper output arm 302A and is vertically secured against the first support ledge 306A. Note, as shown in FIG. 3D, for illustrative purposes, the first end 104A is slightly above the first support ledge 306A; when fully inserted and positioned, the first end 104A would be pressed against the first support ledge 306A. Comparable second, third, and fourth support ledges 306B, 306C, and 306D are located and part of the first input arm 305A, the second input arm 305B, and the lower drain arm access 302B. The first, second third, and fourth support ledges 306A, 306B, 306C, and 306D, respectively limit the extent or distance the corresponding first riser 104, first input arm connector 307A, second input arm connector 307B, and lower drain arm connector 307C engage the upper output arm 302A, the first input arm 305A, the second input arm 305B, and the lower drain arm access 302B, as shown in FIG. 3A and FIG. 3B.

The inner diameter 312 of the lower drain arm access 302B is fractionally greater than the outer diameter 317 of the lower drain arm connector 307C. The first end 313A of the lower drain arm connector 307C engages the receptacle end 314 of the lower drain arm access 302B. The second end 313 of the lower drain arm connector 307C is the low point of the entire tube system 102; thus, condensate may accumulate at the second end 313. The second end 313B is closed by a removable cap (or plug) 318 to facilitate draining the tube system 102 and cleaning and sanitizing the frame connector 301.

The second end 104B of the first riser 104 engages the first, receptacle end 105A of the riser connector 105 and is secured by a mechanical fastener (rivet) 404A or adhesive material. The first end 106A of the second riser 106 engages the second, receptacle end 105B of the riser connector 105 and is also secured by a mechanical fastener (rivet) 403B or adhesive material. The second end 106B of the second riser 106 engages the first, receptacle end 107A of the adjustable tube connector 107, and the first end 108A of the adjustable tube 108 engages the second, receptacle end 107B of the adjustable tube connector 107 and is secuely held by friction. A mask hose 115 connects the second end 108B of the adjustable tube 108 to the CPAP mask 118.

The CPAP pump hose 116 connects the CPAP air pump (not illustrated) to the pipe system through physical/functional connection of the output end 116A of the CPAP pump hose 116 with the input end 320A of the first input arm connector 307A. A supplemental input hose 117 may be connected may be connected to the pipe system 102 to adjust humidity or introduce other therapeutic materials into the flow of air delivered through the CPAP air mask 118. The output end 117A of the hose from the source of supplemental, therapeutic material is physically and functionally introduced into the input end 320B of the second input arm connector 307B.

One skilled in the art recognizes that for propere function of a CPAP system, air flow and pressure from the CPAP pump through the CPAP pump hose 116 through the first input arm connector 307A, and ultimately to the CPAP mask must be maintained within prescribed limits; thus, when supplemental materials are introduced to the second input arm connector 307B, air pressure and flow must be regulated to compensate for the materials introduced so as to maintain the prescribed flow. Such adjustment may involve the source of initial delivery of the supplemental material (for example, an atomizer or cartridge), the CPAP air pump, or both). In addition, when supplemental material is not being introduced through the second input arm connector 307B, the output end 117A of the hose from the source of the supplemental material should be disconnected from the input end 320B of the second input arm connector and the second input arm connector 307B closed with an appropriate cap or plug to avoid loss of the prescribed air flow or pressure to the CPAP mask.

Figure 4:
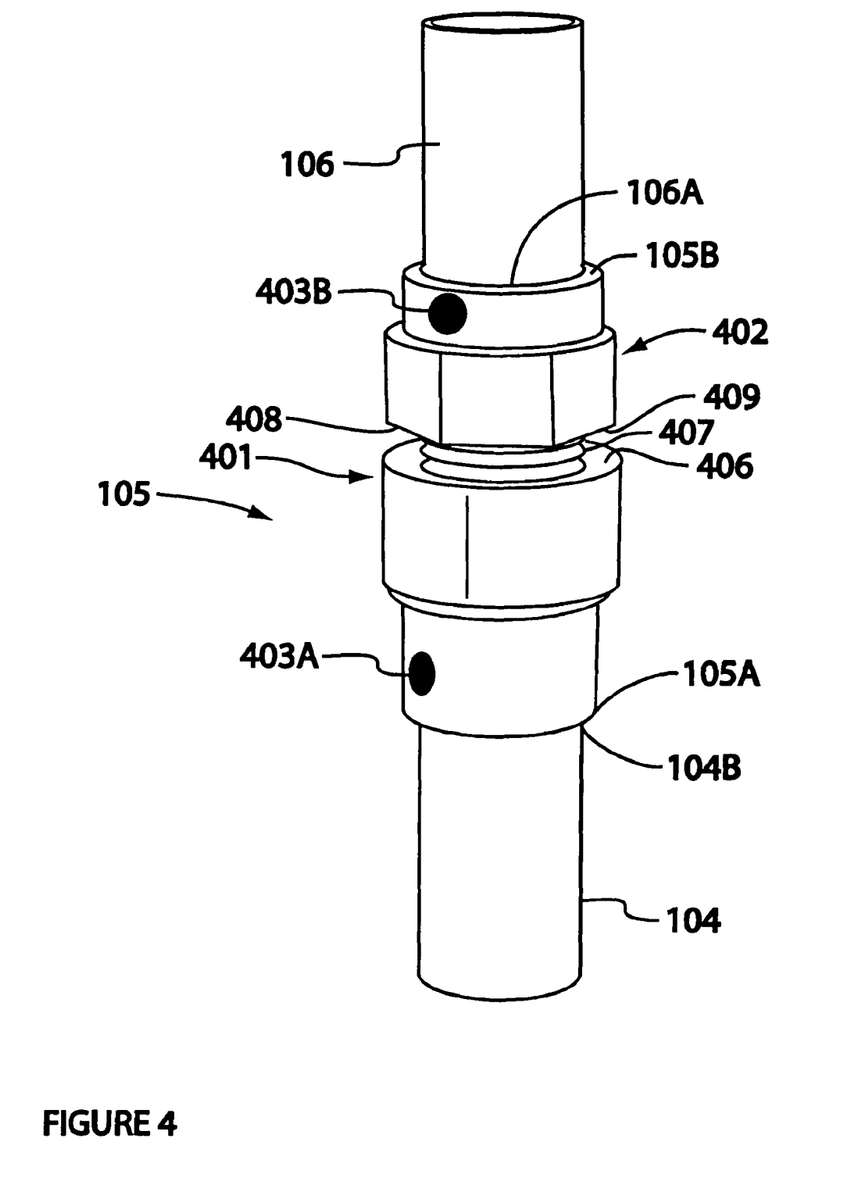
FIG. 4 illustrates details of the first riser with the riser connector.

The riser connector 105, as illustrated in FIG. 4, comprises a lower segment 401 and an upper segment 402. The second end 104B of the first riser 104 engages the first end 105A of the riser connector 105 and secured by a rivet 403A. One of average skilled in the art understands that this connection could be made with appropriate means, including welding/ adhesives other mechanical connectors such as machine (metal) screws.

The first end of 106A of the second riser 106 physically engages the second end 105B of the riser connector 105 and is secured by a rivet 403B or other appropriate means.

The lower segment 401 of the riser connector 105 is connected mechanically (by threads) to the upper segment 402. As shown in FIG. 4, the distal end 406 of the lower segment 401 comprises the male, threaded segment 407, and the proximal end 408 of the upper segment 402 comprises the female, threaded receptacle 409. Engaging the male threaded segment 407 with the female threaded receptacle 406 securely connects the lower 401 and upper 402 segments of the riser connector 105. The lower 401 and upper 402 segments are simply separated by disengaging the male threaded segment 408 and female threaded receptacle 408. This can be accomplished manually, without any tools.

Figure 5:
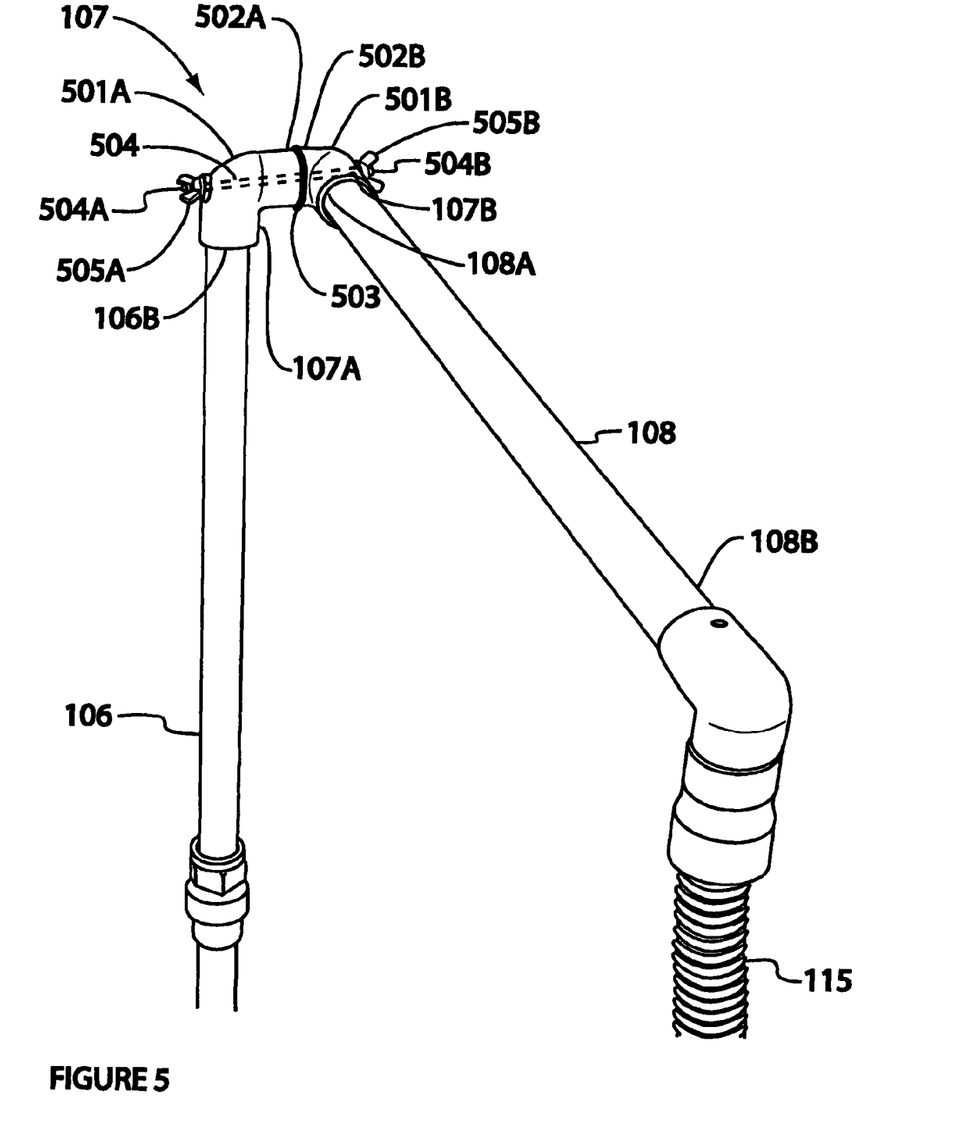
FIG. 5 illustrates details of the adjustable connector.

The adjustable connector 107 (FIG. 5) comprises a fixed, first section 501A and a rotatable, second section 501B. The first end 502B of the rotatable, second section 501B is inserted into the first end 502A of the section 501A. An O-ring 503 seals the interface of the two sections 501A and 501B. A threaded rod 504 traverses adjustable connector 107 and secures the connection between the first 501A and second, rotatable 501B sections by adjustable wing nuts (or comparable fasteners, such as thumb screws) threaded fasteners) threaded on the exposed first and second ends 504A and 504B of the threaded rod 504. The second end 106B of the second pipe section 106 is inserted into the first end 107A of the adjustable connector 107 and secured by a rivet, adhesive or comparable means, and the first end 108A of the pipe arm 108 is inserted into the second end 107B of the adjustable connector 107 and secured with a rivet, adhesive, or comparable means. The relative vertical orientation of the pipe arm 108 to horizontal can be changed by raising or lowering the second end 108B of the adjustable tube 108, thereby adjusting the pitch of the adjustable tube 108 and the relative length of the CPAP mask hose connected to the second end 108B of the adjustable tube 108.

By way of illustration and not limitation, the various parts of the CPAP tube delivery system may be fabricated from a variety of materials. The first 104 and second riser and adjustable tube 108 are fabricated from aircraft grade aluminum (i.e. 6061 T-6 aluminum); such material is generally available from United States suppliers, well known to those skilled in the art. Stainless steel tubing is also appropriate, and plastic, such as PVC pipe, is acceptable but not generally preferred. Both the T-configuration 301A and the cross-configuration 301B of the connector box 301 are manufactured from plastic, commonly PVC and related materials and are found ready made from wholesale plumbing supply sources and similar vendors. Metals, such as stainless steel or aircraft grade aluminum is also suitable, but may require special fabrication of the part. The first riser connector 105 and the adjustable tube connector are fabricated from plastic and generally ready made from plumbing and other outlets in the United States. The also may be fabricated from aircraft grade aluminum and stainless steel. The first 307A and second 307B input arm connectors are made from plastic pipe, as is the lower, drain arm connector, although aircraft grade aluminum and stainless steel are preferred. Generally, commercially available tubes and connectors have suitable inner and/or outer diameters to facilitate connecting or engaging parts, such as, for example, the first end 110 of the first riser 104 and the receptacle end 308 of the upper, out put arm 308. Hoses and hose connectors are available through a variety of medical/home health suppliers, including on-line sales.

The support frame 109 can be manufactured from a variety of materials including wood with various finishes, plastics, and metals. For home use, wood may be acceptable; for clinical settings, plastic and metals are for ease of cleaning and sanitation. As noted above, the anchor is fabricated from a thin metal rod or very stiff wire.

By way of examples, not of limitation, dimensions of the parts are in the following ranges, with actual values frequently established by practical considerations, including materials, costs, and compatible inner and outer diameters of parts that are engaged as described above. Lengths of the first riser 104, second riser 106, and adjustable tube 108 are frequently equal and vary from 14 to 20 inches 35.6 to 50.8 cm. Outside diameter varies from 0.75 to 1.0 inch (1.91 to 2.54 cm) and is selected, as noted to facilitate friction tight engagement of connected parts. The inside diameter of the output arm 302A, the riser connector 105 and the access drain arm varies as noted from slightly less than 0.75 inch to about 1.05 inch (1.85 to 2.60 cm). The inside diameter of the first and second input arm 305A and 305B is slightly greater than or equal to the diameter of first and second input arm connectors 307A and 307B. The input arm connectors are generally fabricated from plastic and vary in length from 3 to 5 inches (7.6 to 12.7 cm) with an outside diameter of about 0.81 to 0.94 inch (2.06 to 2.39 cm).

Figure 6:
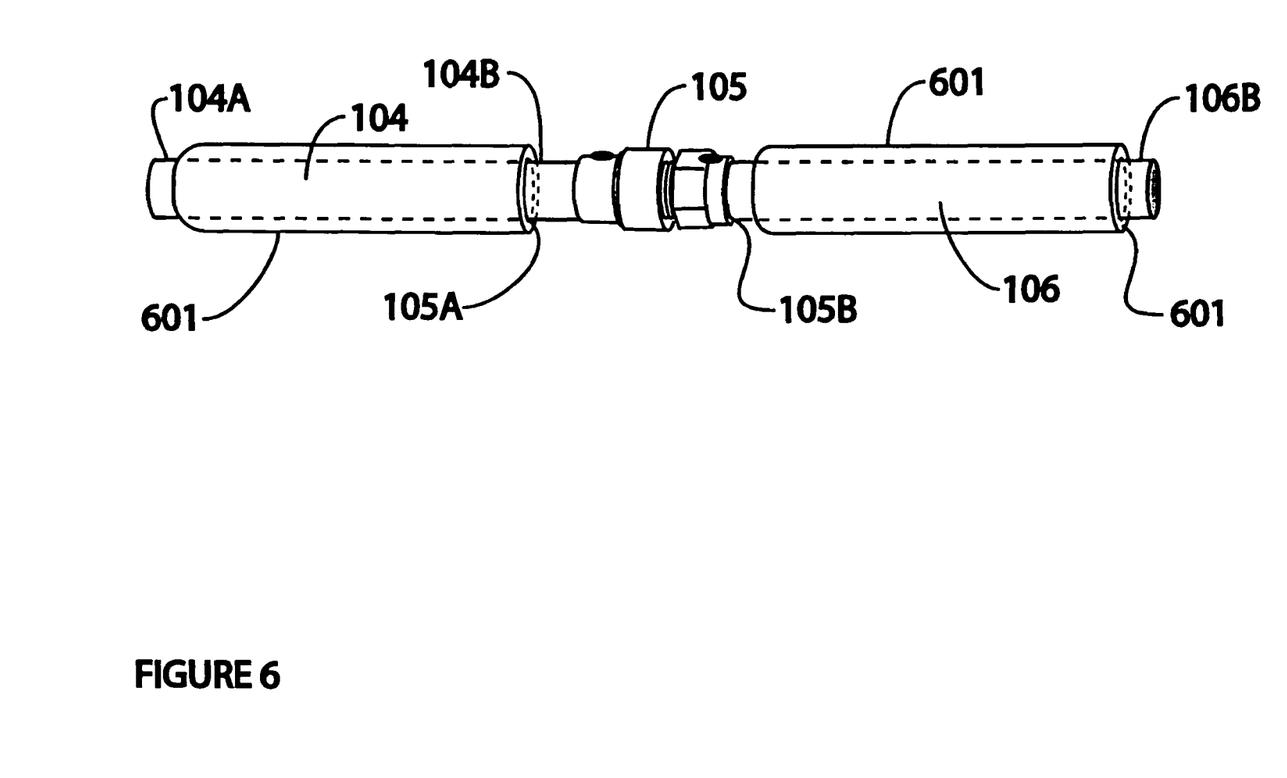
FIG. 6 illustrates insulation of the risers and adjustable tube.

As a product of condensation, moisture may accumulate along the first 104 and second 106 risers and the adjustable tube 108. The condition is most pronounced when the risers, 104 and 106, and adjustable tube 108 are fabricated from metal, such as aircraft aluminum, compared with a plastic, such as PCV. FIG. 6 illustrates the use of an insulation layer to remedy the problem with respect to the first 104, and second 106 risers and the adjustable tube 108.

The riser connector 105 is not insulated (and as one skilled in the art understands, although not shown, neither is the adjustable tube connector 107. The first 104 and second 106 risers are covered/coated with an insulation material 601. A variety of such materials is widely known and readily available through plumbing/air conditioning and larger hardware stores and suppliers. The first 104A and second 104B ends of the first riser are not insulated to allow engagement/positioning with corresponding connectors 103 and 105. Similarly, the first end 106A and the second end 106B of the second riser 106 are not insulated. As shown in FIG. 6, the second end 104B of the first riser 104 engages the first end 105A of the riser connector 105, and the second end of the riser connector 105B engages the first end 106A of the second riser 106. One skilled in the art understands that a wide variety of insulation material suitable for the above is available from plumbing and heating and hardware suppliers. Such material includes, but is not limited to spray-on plastic and foams, dips, and sleeve pull-over materials as well as insulated tape all readily available for general use.

The preceding descriptions, dimensions, and examples illustrate specific modes of the invention. The various parts, descriptions, and examples can be separated and/or combined to yield additional examples all of which are anticipated by the scope and purpose of the invention; thus construction of the following, appended claims should be accorded scope and breadth greater than the modes specifically illustrated.

I claim:

1. A CPAP tube delivery device comprising:
   a tube system,
   a frame connector, and
   a support frame;
   wherein, said tube system comprises a first riser, a riser connector, a second riser, an adjustable connector, and an adjustable tube; wherein said frame comprises a four-sided, open, box-shaped structure, wherein said four-sided, open, box-shaped structure comprises a bottom, a first side, a second side, and a top; wherein said top comprises a first traverse passage, said first and said second sides, respectively comprise a second and a third traverse passage, and said bottom comprises a fourth traverse passage; and wherein said frame further comprises an anchor, wherein said anchor comprises a bridge section, wherein a first and a second anchor leg extend parallel from opposite ends of said bridge section, and further, wherein the ends of said first and of said second anchor leg individually engage and are secured in a corresponding first and second anchor socket; and further wherein said frame connector comprises a connector body, wherein said connector body comprises a vertical axis and element and a horizontal axis and element, and wherein said vertical axis and element comprise an upper, output arm and a lower drain access arm; and further wherein said horizontal axis and element comprises at least a first input arm, wherein said body connector assumes a T-configuration; and further wherein the interior of said body connector is defined and limited by the interior wall surface, wherein said interior comprises a contiguous, open chamber; and further, wherein a support ledge circumscribes said interior wall surface of said upper output arm, said lower drain access arm, and said at least at first input arm; and wherein said frame connector comprises at least a first input arm connector, wherein the first end of said first input arm connector engages the connector end of said first input arm and is secured against the second support ledge, and further, wherein the first end of the lower, drain arm connector engages the receptacle end of said lower, drain access arm and is secured against the third support ledge, and, wherein, a removable cap closure device is secured to the second end of said lower drain connector; and further, wherein the first end of the first end of the first riser engages the receptacle end of said upper output arm and is secured against said first support ledge; and further, wherein the second end of said first riser engages and is connected to the first end of the first riser connector, and the first end of the second riser engages and is connected to the second end of said first riser connector, and the second end of said second riser engages and is connected to the first end of the adjustable tube connector, and the first end of the adjustable tube engages and is connected to the second end of said adjustable tube connector, and the first end of a mask hose is connected to the second end of said adjustable tube by a first hose connector, and wherein a first end of a CPAP pump hose is connected to a second end of said first riser connector and said the second end of said CPAP hose is connected to a CPAP pump.

2. The CPAP tube delivery device of claim 1 wherein the connector body comprises a T-configuration.

3. The CPAP tube delivery device of claim 1 wherein the connector body comprises a cross-configuration.

4. The CPAP tube delivery device of claim 1 wherein the support frame is made from wood.

5. The CPAP tube delivery device of claim 1 wherein the support frame is made from a plastic materials.

6. The CPAP tube delivery device of claim 1 wherein the frame is made from metallic materials, including alloys.

7. The CPAP tube delivery device of claim 1 wherein the first and second risers and the adjustable tube are made from aircraft aluminum.

8. The CPAP tube delivery device of claim 1 wherein the first and second risers and the adjustable tube are made from stainless steel.

9. The CPAP tube delivery device of claim 1 wherein the first and second risers and the adjustable tube are insulated.

10. The CPAP tube delivery device of claim 1 wherein the first and second risers and the adjustable tube are made from plastic materials.

\* \* \* \* \*